(12) United States Patent
Berry et al.

(10) Patent No.: US 7,285,134 B2
(45) Date of Patent: Oct. 23, 2007

(54) VERTEBRAL BODY REPLACEMENT IMPLANT

(75) Inventors: Bret M. Berry, Jacksonville, FL (US); Eric C. Lange, Germantown, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 90 days.

(21) Appl. No.: 10/691,256

(22) Filed: Oct. 22, 2003

(65) Prior Publication Data
US 2005/0090898 A1    Apr. 28, 2005

(51) Int. Cl.
*A61F 2/44* (2006.01)
(52) U.S. Cl. .................. 623/17.11; 623/17.16
(58) Field of Classification Search .......... 623/17.14, 623/17.16, 17.11
See application file for complete search history.

(56) References Cited

U.S. PATENT DOCUMENTS

| | | | | |
|---|---|---|---|---|
| 4,401,112 A | * | 8/1983 | Rezaian | 606/61 |
| 4,553,273 A | * | 11/1985 | Wu | 623/23.45 |
| 4,599,086 A | * | 7/1986 | Doty | 606/61 |
| 4,657,550 A | * | 4/1987 | Daher | 623/17.11 |
| 5,236,460 A | * | 8/1993 | Barber | 623/17.15 |
| 5,290,312 A | * | 3/1994 | Kojimoto et al. | 623/17.15 |
| 5,571,192 A | * | 11/1996 | Schonhoffer | 623/17.11 |
| 5,702,449 A | * | 12/1997 | McKay | 623/17.16 |
| 5,702,453 A | | 12/1997 | Rabbe et al. | |
| 5,702,455 A | * | 12/1997 | Saggar | 623/17.15 |
| 5,723,013 A | * | 3/1998 | Jeanson et al. | 623/17.16 |
| 5,776,197 A | | 7/1998 | Rabbe et al. | |
| 5,776,198 A | | 7/1998 | Rabbe et al. | |
| 5,865,846 A | * | 2/1999 | Bryan et al. | 128/898 |
| 5,895,428 A | * | 4/1999 | Berry | 623/17.15 |
| 5,989,290 A | * | 11/1999 | Biedermann et al. | 623/17.11 |
| 6,015,436 A | * | 1/2000 | Schonhoffer | 623/17.16 |
| 6,086,613 A | * | 7/2000 | Camino et al. | 623/17.16 |
| 6,190,413 B1 | * | 2/2001 | Sutcliffe | 623/17.11 |
| 6,200,348 B1 | * | 3/2001 | Biedermann et al. | 623/17.11 |
| 6,296,665 B1 | * | 10/2001 | Strnad et al. | 623/17.16 |
| 6,344,057 B1 | | 2/2002 | Rabbe et al. | |
| 2002/0169507 A1 | * | 11/2002 | Malone | 623/17.11 |
| 2004/0172129 A1 | * | 9/2004 | Schafer et al. | 623/17.11 |

OTHER PUBLICATIONS

Medtronic Sofamor Danek, "Verte-Span—Vertebral Body Replacement Device", 2001, brochure.
ISA/EP International Search Report for PCT/US2004/034333; Jun. 3, 2005.

* cited by examiner

*Primary Examiner*—Alvin J. Stewart
(74) *Attorney, Agent, or Firm*—Haynes and Boone, LLP

(57) ABSTRACT

A vertebral replacement implant assembly for inserting in a space left by one or more removed vertebrae between adjacent intact vertebrae, according to which at least two elongated members are disposed in the space and a connector member is connected between adjacent elongated members in a manner so that a dimension of the assembly thus formed can be varied. Further, a graft containment device for use with a vertebral implant.

13 Claims, 6 Drawing Sheets

VERTEBRAL BODY REPLACEMENT IMPLANT

FIELD OF THE INVENTION

The present invention relates generally to an implant for replacement of one or more vertebral bodies and their adjacent disks, and more particularly, to implant components that permit optimal anatomy accommodation and facilitate grafting.

BACKGROUND

A variety of spinal injuries and deformities can occur due to trauma, disease, or congenital effects. These injuries and deformities can, ultimately, result in the destruction of one or more vertebral bodies. One type of spinal deformity, a kyphosis, involves a prolapse of the vertebral column towards the front of the body, often caused by the destruction of the vertebral body itself. This destruction can be in the form of a trauma type injury, such as a fracture or burst injury to the vertebral body, or a non-traumatic deformity caused by a tumor or a degeneration of the bone in the vertebral body.

In most treatments of a kyphosis, a high degree of anterior reconstruction of the spine is required, most frequently involving total removal of the damaged vertebral body. In a typical anterior approach, partial or total surgical excision of the vertebral body and the two adjacent vertebral disks is carried out. The remaining space is then distracted to manipulate the spine to its correct orientation. Various forms of reconstruction using an osteosynthesis device, such as a vertebral replacement body, can then be performed in the space created by the removal of the vertebral body and disks. However, existing vertebral body replacement devices permit only limited bone ingrowth, are relatively hard to place, and offer limited adjustability to accommodate a patient's specific vertebral anatomy.

Therefore, a vertebral body replacement is needed that permits greater bone ingrowth, facilitates placement of bone graft between adjacent healthy vertebrae, and allows greater adjustability to accommodate a patient's specific vertebral anatomy.

SUMMARY

The present disclosure relates to a vertebral replacement implant for interposition in a space left by one or more at least partially removed vertebrae between adjacent intact vertebrae. In one embodiment, a first tubular body is sized to span a first portion of the space between the intact vertebrae, and a second tubular body is sized to span a second portion of the space between the intact vertebrae. A connector is connected to corresponding ends of the first and second bodies, and an endplate assembly is attached to the other end of the first body. In another embodiment, a graft containment device is used with the vertebral replacement implant. The graft containment device has an internal cavity, a sidewall, an open upper end, a closed lower end with apertures extending therethrough, and an engagement device for maintaining the containment device within the cavity of the vertebral replacement implant.

BRIEF DESCRIPTION OF THE DRAWINGS

FIG. 6b is a perspective view of the assembled assembly shown in FIG. 5a.

FIG. 7b is a perspective view of the assembly shown in FIG. 6a.

DETAILED DESCRIPTION

Figure 1:
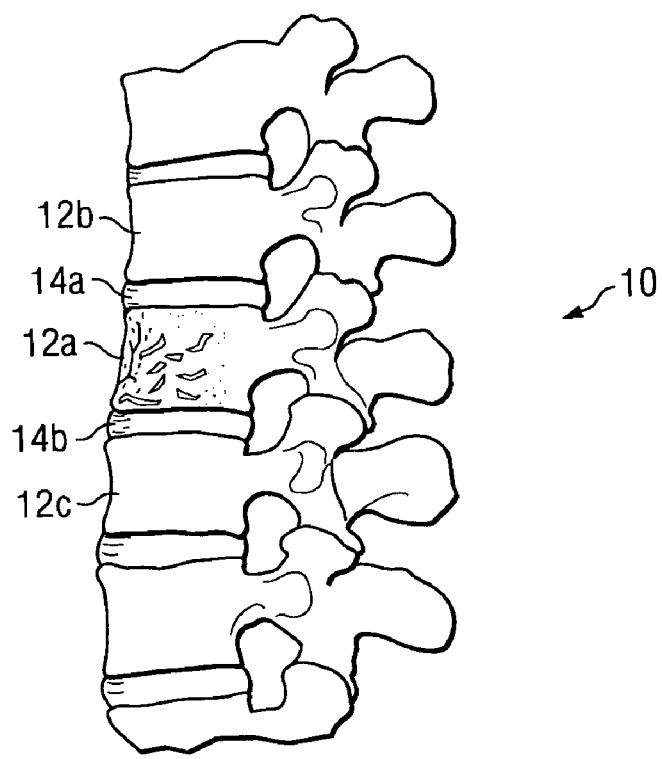
FIG. 1 is an perspective view of a destroyed vertebral body within a vertebral column.

Referring first to FIG. 1, the reference numeral 10 refers to a vertebral column with a damaged vertebra 12a extending between two intact vertebrae 12b and 12c. A disk 14a extends between vertebrae 12a and 12b, and a disk 14b extends between vertebrae 12a and 12c. In a typical surgical excision, a major portion of the vertebra 12a is removed together with disks 14a and 14b creating a void between the two intact vertebra 12b and 12c. A vertebral body replacement according to an embodiment of the present invention is provided to fill the void between the two intact vertebrae 12b and 12c.

Figure 2:
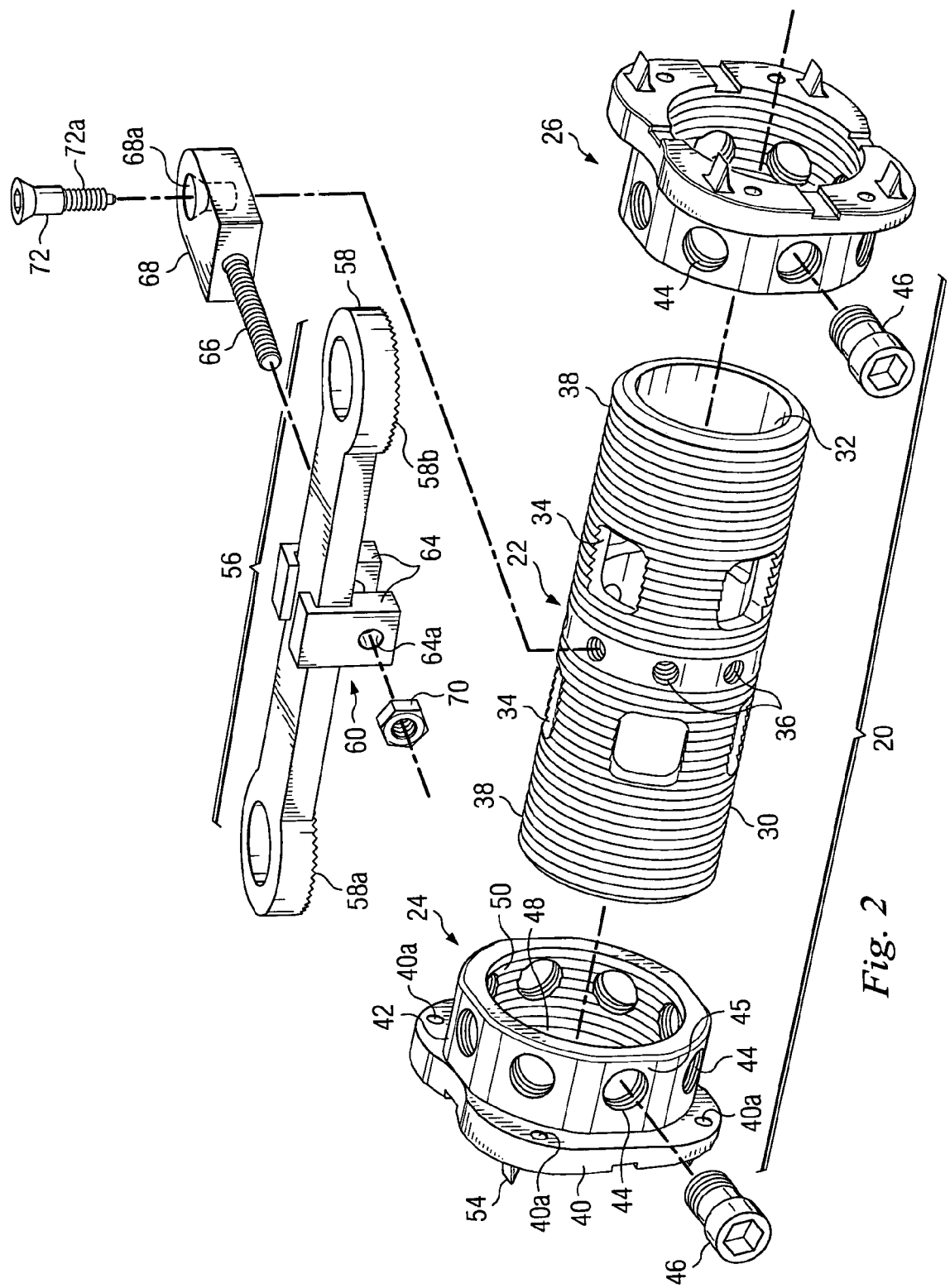
FIG. 2 is an exploded perspective view of a vertebral body replacement assembly according to one embodiment of the present invention.

Referring now to FIG. 2, a vertebral body replacement assembly according to an embodiment of the present invention is referred to, in general, by the reference numeral 20 and includes tubular body 22 connected between two endplate assemblies 24 and 26 in a manner to be described. The body 22 defines a hollow bore 32 therethrough which is configured to receive an implantable material, typically bone osteosynthesis material (not shown), which may be in the form of autogenous, allograft or synthetic bone void filler material.

The tubular body 22 is provided with a plurality of angularly and axially spaced apertures 34 in communication with the bore 32. The apertures 34 provide a path for bone or tissue ingrowth and vascularization to further enhance the stability of the implant. As specifically shown in FIG. 2, the apertures 34 are large enough and are positioned such that graft material can be packed, with maximum surgical accessibility, into the body 22 after the assembly 20 is installed and adjusted in a manner to be described. In one embodiment, the apertures 34 may extend between 28% and 46% of the length of the body 22, allowing as much opening as possible for the placement of graft material. After surgical installation, at least one aperture 34 is accessible to allow graft material to be packed into the body 22. To permit monitoring of the healing process and to determine whether bone formation has advanced through the body 22, the apertures 34 may be aligned angularly to permit x-ray visualization through the apertures 34.

A plurality of angularly spread threaded apertures 36 are formed through the body 22 generally in the middle of the body 22, for reasons to be described.

External threads 38 are formed on the outer surface of the tubular body 22 and may extend for substantially the entire length of the body. In some embodiments, the external threads 38 may extend from the ends of the tubular body 22 to the apertures 34. Since the primary load on the body 22 will be in axial compression, rather than bending, the wall forming the body 22 can be relatively thin, such as approximately one (1) mm thick.

The endplate assembly 24 includes a flange 40, which can cover a substantial load-bearing area of the corresponding end face of the adjacent intact vertebral body (FIG. 1). A hollow cylinder 42 is integrally formed with the flange 40 and includes a number of angularly spaced threaded openings 44 with each being adapted to receive a set screw 46 therein. The cylinder 42 and the flange 40 of the endplate assembly 24 define a through bore 48, the inside surface of which is provided with internal threads 50 which extend along the entire length of the cylinder 42 and into the flange 40 as necessary. The threads 50 are configured to mate with the external threads 38 of the corresponding end portion of the body 22 to connect the body to the endplate assembly 24.

A plurality of angularly spread vascularization apertures 40a extend through the flange 40 to promote tissue growth in the space between the adjacent vertebrae. One or more spikes 54 project outwardly from the end face of the flange 40 and are configured to penetrate the adjacent vertebra to help maintain the position of the implant in situ. The outer surface of the plate assembly 24 may also include a series of flats 45 adjacent the threaded openings 44. In one embodiment, the flats 45 form a hexagonal driving pattern that may be engaged by a surgical tool. The endplate assembly 24 may be angled to create a desired vertebral column alignment.

The endplate assembly 26 is identical to the assembly 24 and therefore will not be described in detail. Further details and embodiments of the endplate assemblies 24 and 26 are disclosed in U.S. Pat. Nos. 5,702,453; 5,776,197; 5,776,198; and 6,344,057 B1 to Rabbe et al. ("the Rabbe patents") which are incorporated herein by reference.

Figure 3:
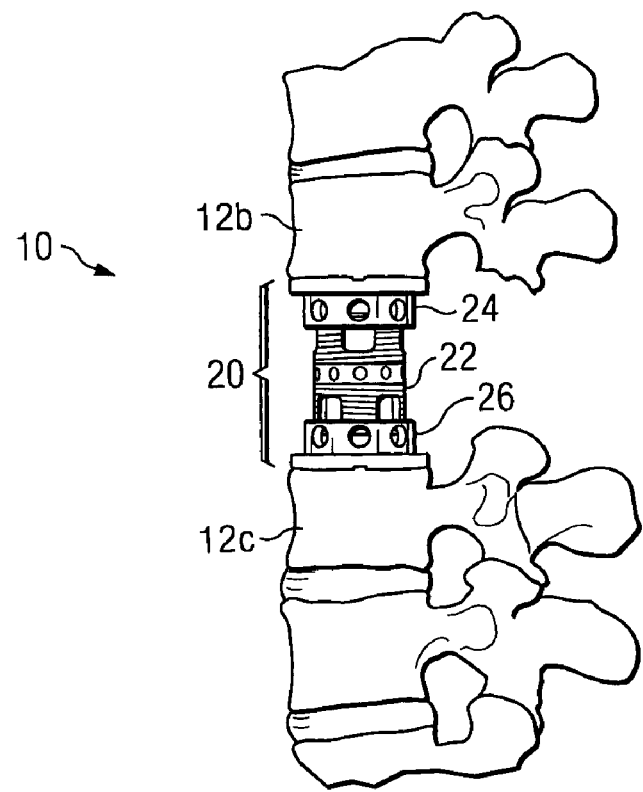
FIG. 3 is a perspective view of a vertebral body replacement disposed within the vertebral column of FIG. 1.

It is understood that the dimensions of the tubular body 22 and/or the end plate assemblies 24 and 26 can vary in accordance with size of the vertebral column 10. Once these dimensions have been selected for a particular patient, each of the endplate assemblies 24 and 26 is threaded onto the body 22 until a desired height is attained so as to fit in the vertebral column 10 assuming that the disks 14a and 14b are removed, as shown in FIG. 3. To this end, and referring to FIG. 2, the external threads 38 on the body 22 are cut in opposite directions so that the endplate assemblies 24 and 26 can be drawn together or apart by rotating only the body. The advantage of this arrangement is that it is easier to adjust the height of the total assembly 20 to fit in the vertebral column 10 while maintaining the proper orientation of the endplate assemblies 24 and 26. Alternatively, the cut of the threads 38 can be the same at each end of the body 22 so that the endplate assemblies 24 and 26 are rotated in opposite directions onto the body 22. An advantage of the latter arrangement is that in situ the assembly is unable to unthread itself.

After the end portions of the body 22 are threaded into endplate assemblies 24 and 26, one or more set screws 46 are threaded into an opening or openings 44 of the assemblies 24 and 26 to fix each of the assemblies to a corresponding end of the tubular body 22. The set screw(s) 46 exert a clamping pressure against the body 22 to hold it in place and prevent its rotation with respect to the endplate assemblies 24 and 26. Each set screw 46 can be a breakable locking screw in which the head of the screw shears off when the tightening torque limit is reached. Such a locking screw is disclosed in U.S. Pat. No. 6,478,795, the disclosure of which is incorporated by reference.

A support assembly 56 is provided to engage the body 22 and the endplate assemblies 24 and 26 to ensure that the assembly 20 will not migrate after installation. The support assembly 56 includes a stabilization plate 58 having two circular ends 58a and 58b the bottom faces of which can be serrated, or roughened, to mate with installation devices (not shown) as described in detail in the above-cited Rabbe patents. A clamp assembly 60 is provided and includes a pair of clamp halves 64 which extend to the respective sides of the plate 58 and which are preferably C-shaped to firmly grip and support the plate. Each of the clamp halves 64 includes an aperture 64a which receives a threaded rod 66 extending from one end of a base 68. A nut 70 is threaded on the rod 66 and can be rotated to draw the clamp halves 64 together about the stabilization plate 58. An aperture 68a extends through the base 68 and receives a locking screw 72 which includes a threaded shank 72a which is adapted to engage one of the threaded apertures 36 in the body 22 to secure the support assembly 56 to the body.

Figure 4:
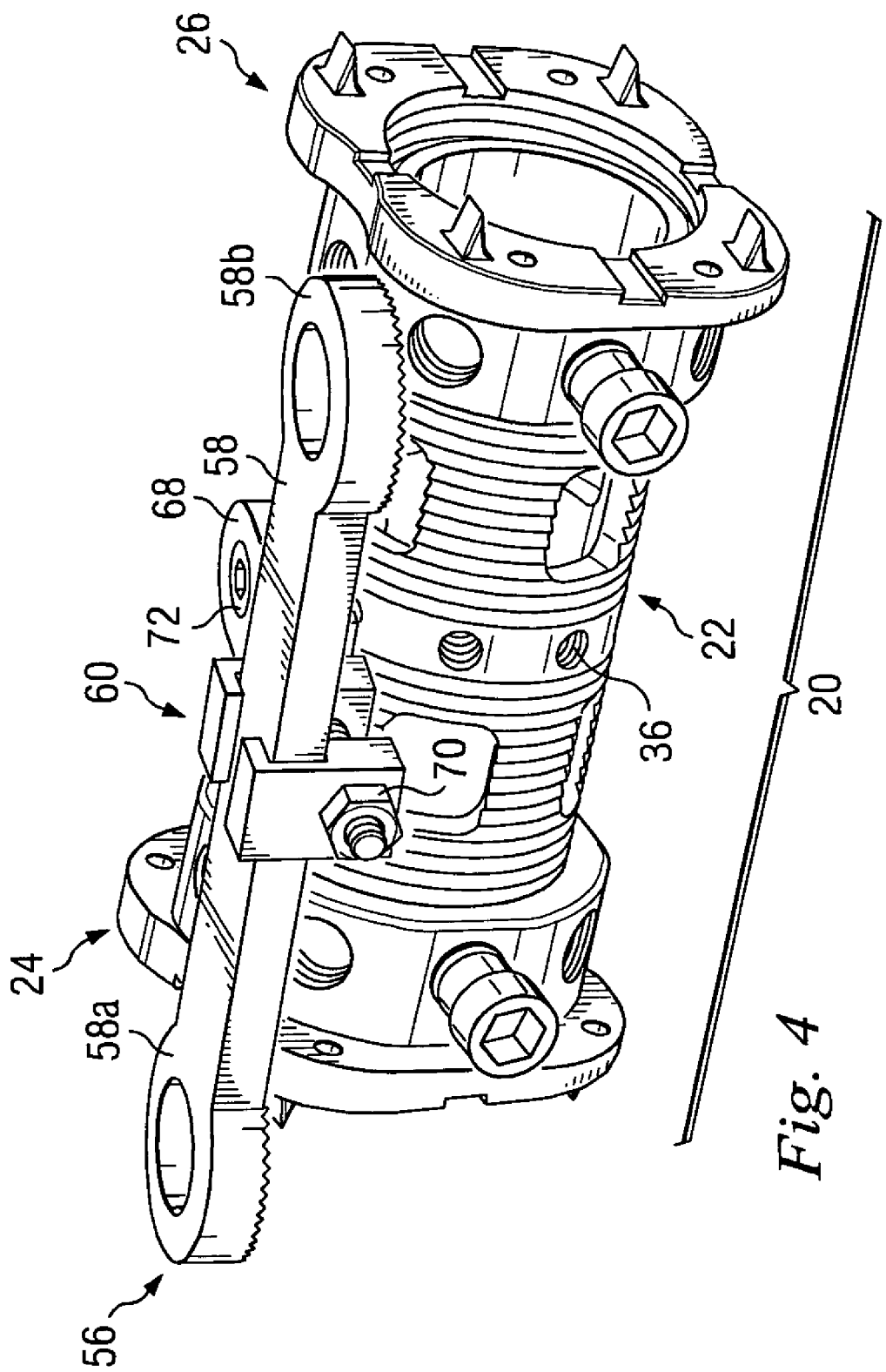
FIG. 4 is perspective view of the assembled vertebral body replacement assembly of FIG. 2.

FIG. 4 depicts the components of FIG. 2 in an assembled condition. In particular, the endplate assemblies 24 and 26 are threaded over the respective threaded end portions of the body 22 until the desired height of the assembled components is achieved, as discussed above. The clamp halves 60 are attached but not clamped to the stabilization plate 58 which is spaced laterally from the assembly 20, and the assembly thus formed is disposed between the intact vertebra 12b and 12c (FIG. 3). The circular ends 58a and 58b of the plate 58 are then attached to the intact vertebrae 12b and 12c in a manner described in detail in the above-cited Rabbe patents. The clamp halves 60 are then moved along the length of the plate 58 until the aperture 68a of the base 68 is aligned with an appropriate one of the threaded apertures 36 in the threaded body 22. As so aligned, the locking screw 72 can then be easily threaded through the aperture 68a and into one of the apertures 36 to secure the base 68 to the body 22. The clamp halves 60 are then fully clamped onto the plate 58 by tightening the nut 70 on the threaded rod 66 to secure the assembly 20 in the vertebral column 10. It is noted that FIG. 3 depicts the vertebral body replacement assembly 20 of FIG. 2 inserted in the vertebral column 10 of FIG. 1 with the support assembly 56 not being shown in the interest of clarity.

Figure 5:
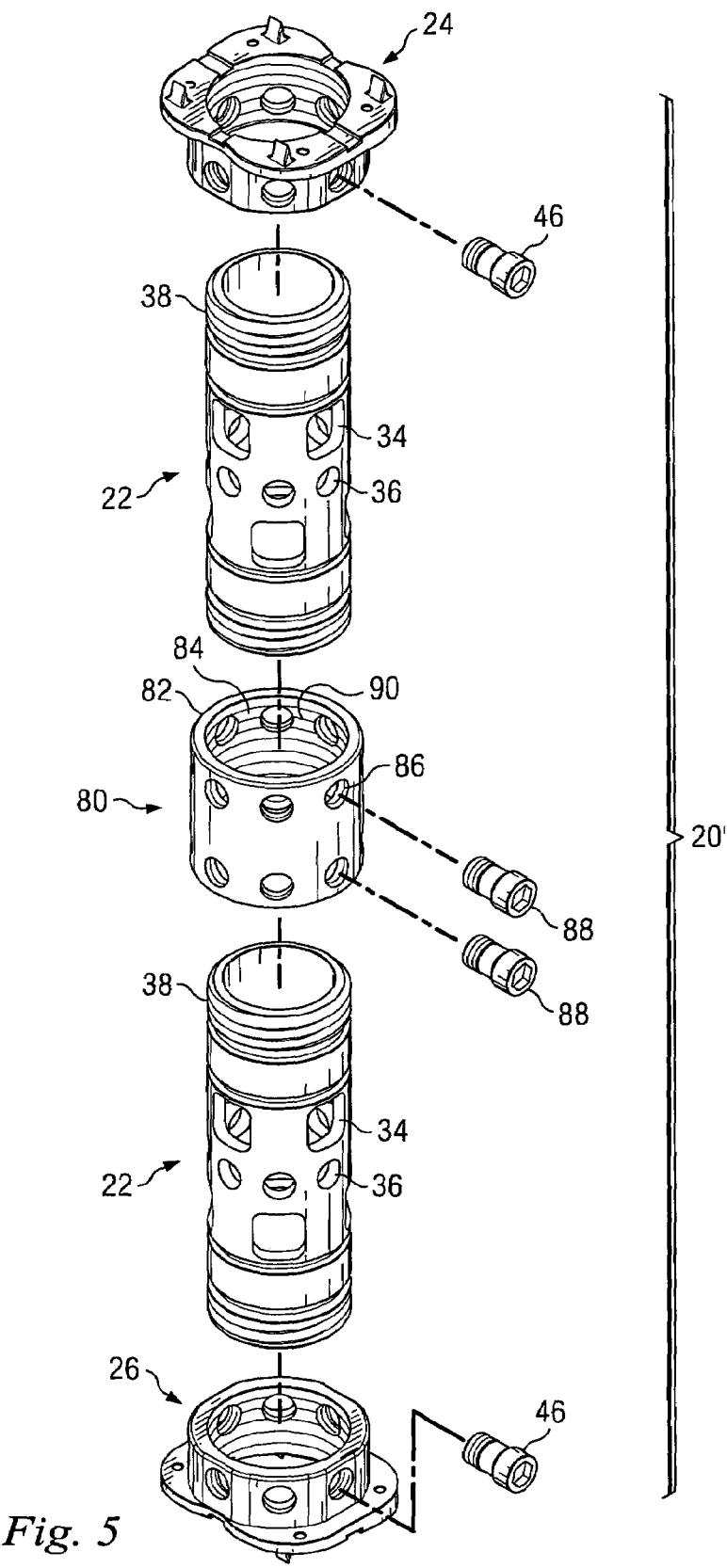
FIG. 5 is an exploded perspective view of a vertebral body replacement assembly according to a second embodiment of the present invention.

FIG. 5 depicts a vertebral body replacement assembly 20' according to a second embodiment of the present invention. The assembly 20' includes two tubular bodies 22 similar to the embodiment of FIG. 2 connected to a tubular connector 80 to achieve an extended vertebral height. The connector 80 is formed from a generally cylindrical enclosure 82 which defines a bore 84 therethrough. The bore 84 may receive bone implant material (not shown), which may be in any form as previously described.

The cylindrical enclosure 82 includes a number of threaded openings 86 adapted to receive set screws 88 therein which can be in the form of a breakable locking screw as described above. The inside surface of the bore 84 is provided with internal threads 90 which are configured to mate with the external threads 38 of the tubular bodies 22, so that each opposite end portion of the connector 80 can be threadedly engaged with a body 22. Rotation of the connector 80 thus causes axial movement of both bodies 22 relative to the connector, to vary the height of the assembly 20'.

Once the proper height of the assembly 20' is obtained for the particular patient, the set screws 88 are threaded into an appropriate one of the threaded openings 86 in the connector 80 in order that the set screws 88 extend into contact with the bodies 22 to secure the connector to the bodies. Although only two set screws 88 are depicted, it is understood that additional set screws can be used, as needed.

After the connector 80 has been connected between the bodies 22 as described above, each of the endplate assemblies 24 and 26 is threaded onto its corresponding body 22 until the desired height is attained. The set screws 46 are then threaded into corresponding openings 44 in each of the endplate assemblies 24 and 26 to attach the latter assemblies to the bodies 22 in the manner described above. It is understood that the connector 80, the bodies 22 and the endplate assemblies 24 and 26 can all be threadedly engaged to achieve the desired height before the set screws 88 and 46 are used to secure the bodies 22. Further, the sequence of tightening set screws to immobilize a threaded interface may be conducted in any order to achieve the desired result.

Figure 6A:
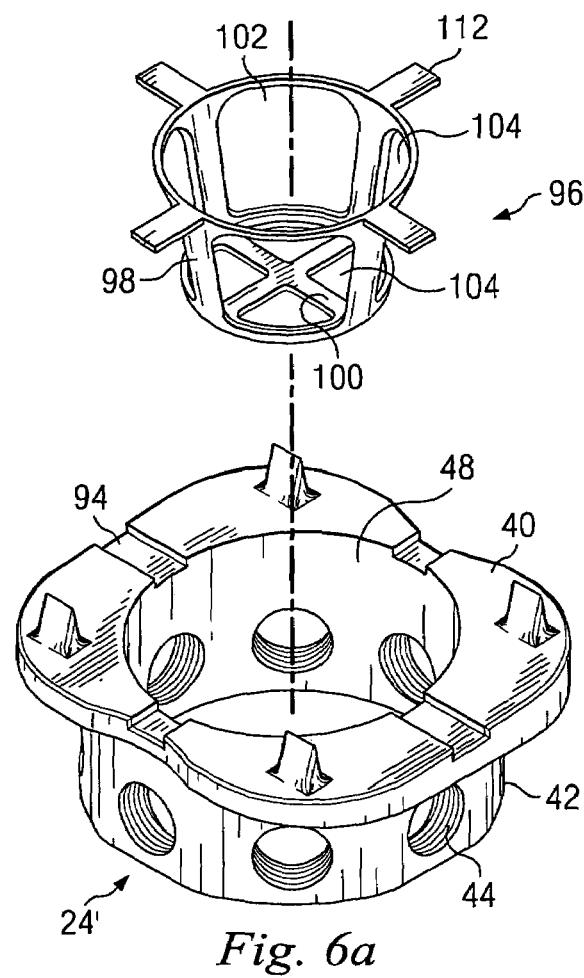
FIG. 6a is an exploded perspective view of an endplate and graft basket assembly in accordance with a first embodiment of the present invention.
Figure 6B:
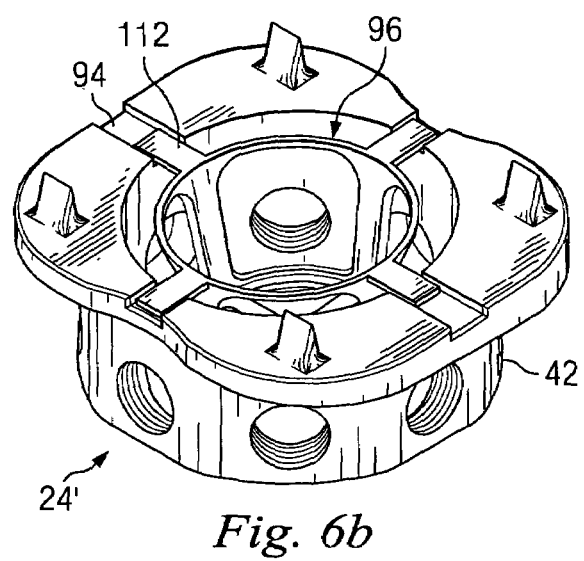

According to the embodiment of FIGS. 6a and 6b, an endplate assembly 24' is provided that includes components that are substantially identical to the components forming the endplate assembly 24, which components are given the same reference numerals. According to the embodiment of FIGS. 6a and 6b, a plurality of angularly spaced recesses 94 are formed in the upper surface of the flange 40, as viewed in FIG. 6a, and the cylinder 42 of the endplate assembly 24' is configured to accept a graft basket 96.

The graft basket 96 is formed by a cylindrical wall 98 and a base 100 having a bottom surface which define a cavity 102 suitable for receiving graft material (not shown). The cylindrical wall 98 need not be perfectly cylindrical but rather may be tapered or angled. The wall 98 and the base 100 are provided with a plurality of apertures 104 suitable to promote tissue ingrowth and vascularization. The apertures 104 may permit a line of sight to form through the apertures 34 of body 22, through the bore 32, and through the basket 96.

The basket 96 is designed to fit entirely within the bore 48 of the cylinder 42, and one or more positioning tabs 112 project outwardly from the cylindrical wall 98 of the basket and into the recesses 94. The recesses 94 are aligned and sized to receive the positioning tabs 112 in a press fit or a snap fit to locate the basket 96 within the cylinder 42 as shown in FIG. 6b.

It is understood that another endplate assembly can also be provided which is similar to the endplate assembly 24' and can be connected as part of the assembly 20 as shown in FIGS. 1-5.

Figure 7A:
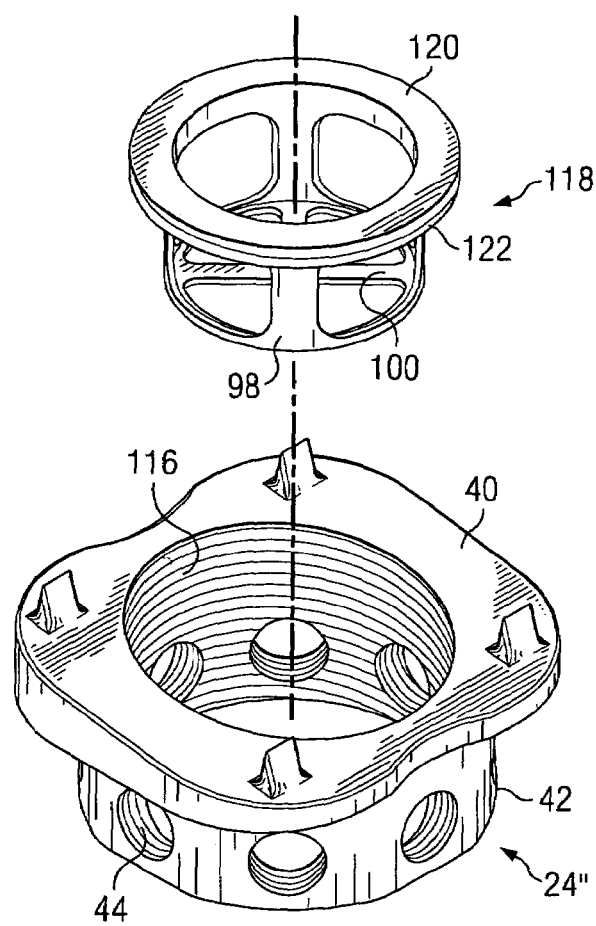
FIG. 7a is an exploded perspective view of an endplate and graft basket assembly in accordance with another embodiment of the present invention.
Figure 7B:
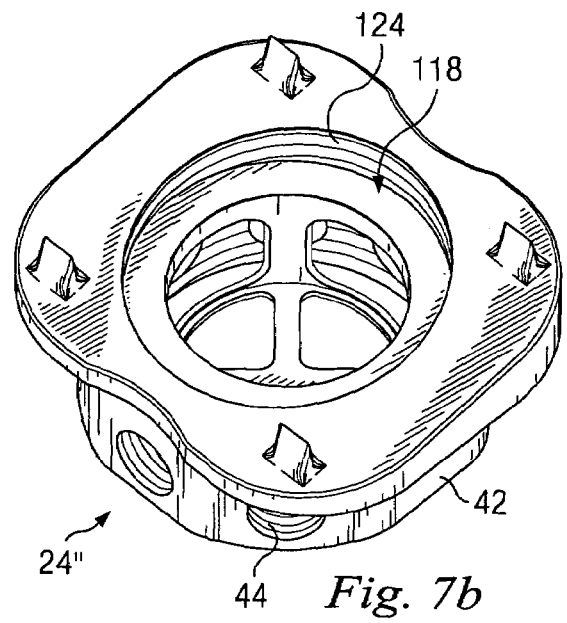

According to the embodiment of FIGS. 7a and 7b, an endplate assembly 24" is provided that includes components that are substantially identical to the components forming the endplate assembly 24, which components are given the same reference numerals. According to the embodiment of FIGS. 7a and 7b, the inner wall of the cylinder 42 is provided with threads 116 and is configured to receive a graft basket 118 which is similar to the basket 96 of the previous embodiment and includes identical components of the latter basket which are given the same reference numerals.

The basket 118 does not have tabs but, rather, has a outwardly extending lip 120 integrally formed with the cylindrical wall 98. The outer circumference of the lip 120 is provided with external threads 122 which threadedly engage the threads 116 of the cylinder 42 to secure the basket 118 in the cylinder, as shown in FIG. 7b. It is understood that another endplate assembly can also be provided which is similar or identical to the endplate assembly 24" and can be connected as part of the assembly 20 as shown in FIGS. 1-5.

Endplate assembly 24' or 24" and its corresponding and opposite endplate assembly may both be threaded sufficiently far onto opposite end portions of the body 22 to permit the assembled components to be inserted into the vertebral column 10. Graft material may be packed into the body 22. The graft baskets 96 or 118 can be fit into the endplate assemblies 24' or 24", respectively, with similar baskets inserted into the corresponding and opposite endplate assembly. The baskets can be filled with implantable graft material which may be osteogenic material or other bone growth promoting material. It is understood the packing of the graft material may occur before or after the endplate assemblies are attached to the body 22. In some embodiments, the baskets 96 and 118 may be sized to extend beyond their respective cylinders 42 and into the body 22, and may even fill the bore 32.

The assembled components may then be inserted into the vertebral column 10 and the endplate assemblies may be advanced toward the intact vertebral endplates thereby engaging the contents of the baskets with the vertebral endplates. As described above, set screws such as 46 may be used to lock the endplate assemblies to the body 22. Additional graft material may be inserted through the apertures 34 of body 22 to further fill the bore 32, including any voids created by advancing the endplate assemblies.

Alternatives

In the embodiment of FIG. 2, the threads 38 on the body 22 can be internal while the threads 50 of the endplate assemblies can be external. In this case, the inner diameter of the body 22 would naturally be slightly greater than the outer diameter of the cylinder of the endplate assemblies. In one alternative embodiment, the hollow cylinder 42 of the endplate assembly 24 may only extend along a portion of the longitudinal axis and only a portion may include threads. In another alternative embodiment, the threads 38 on the body 22 extend over only the end portions of the tubular body 22. Moreover, while threads have been illustrated as a preferred interface, other rotational and non-rotational interfaces may be utilized, for example but without limitation, ratchets, rack and pinion, frictional engagement, and gears. It will be appreciated that with alternative designs, the body 22 and the endplate assemblies may no longer include cylindrical interfaces such that other configurations may be utilized.

To determine, in post surgical examination, whether bone formation has occurred, the apertures 34 may be positioned to permit x-ray visualization through one aperture 34, across the bore 32, and through another aperture 34. For example, there may be an even number of angularly spaced apertures 34, evenly spaced such that a straight line of sight may be formed through two aligned apertures 34.

In the embodiment of FIG. 5, the threads 90 on the connector 80 can be external while the threads 38 on the bodies 22 can be internal.

In FIG. 5, to further increase the overall length of the assembly 20', three or more bodies 22 can be threadedly engaged with connectors 80 between the adjacent bodies 22.

The connector, or connectors 80 can be angled or curved to modify the overall lordosis or kyphosis of the assembly 20'. Still further, at least one end or portion of the body 22 may be angled or curved.

The apertures 104 or other openings in the baskets 96 and 118 may be modified to suit the specific material implanted.

In the embodiment of FIGS. 7a and 7b, the lip 120 may be omitted and external threads may be formed on the outer surface of the cylindrical wall 42.

The graft baskets, such as 96 and 118, maybe formed from a resorbable polymer material. Furthermore, any or all of the components disclosed can be made from any material suitable for implantation.

The above graft basket embodiments are not limited to use with a specific endplate assembly, but are easily applicable to other endplate assemblies such as those described in the above Rabbe patents.

Although only a few exemplary embodiments of this invention have been described in detail above, those skilled in the art will readily appreciate that many modifications are possible in the exemplary embodiments without materially departing from the novel teachings and advantages of this invention. Accordingly, all such modifications are intended to be included within the scope of this invention as defined in the following claims. In the claims, means-plus-function clauses are intended to cover the structures described herein as performing the recited function and not only structural equivalents, but also equivalent structures.

What is claimed is:

1. A vertebral replacement implant for interposition in a space left by one or more removed vertebrae between adjacent intact vertebrae, comprising:
    a tubular body having opposite ends and sized to span at least a portion of the space between the intact vertebrae;
    a pair of endplate assemblies attached to each of the opposite ends of the body, each of the endplate assemblies having an end surface and a tubular portion defining a bore therethrough extending through the end surface; and
    a basket comprising a tubular wall bounded by a base having a bottom surface, the wall and base defining a cavity, wherein the basket is adapted to be disposed within at least one of the bores.

2. The vertebral replacement implant according to claim 1 wherein the cavity is suitable for receiving graft material.

3. The vertebral replacement implant according to claim 1 wherein the basket extends into the tubular body.

4. The vertebral replacement implant according to claim 1 wherein the basket includes at least one positioning tab; and
    wherein the end surface includes at least one positioning recess configured to engage the at least one positioning tab.

5. The vertebral replacement implant according to claim 1 wherein the tubular portion has first threads defined thereon; and
    wherein the basket has second threads thereon configured to threadedly engage the first threads on the cylindrical portion.

6. The vertebral replacement implant according to claim 1 wherein the basket includes one or more apertures.

7. The vertebral replacement implant according to claim 6 wherein the apertures extend over more than 50% of the basket.

8. The vertebral replacement implant according to claim 1, wherein the tubular body includes a wall defining a hollow interior, the wall further defining a plurality of openings therethrough, the openings being in communication with the hollow interior.

9. The vertebral replacement implant according to claim 8, wherein the openings are sized to allow a graft material entry into the hollow interior.

10. The vertebral replacement implant according to claim 8, wherein after the interposition in the space left by one or more vertebrae, at least one of the openings is accessible.

11. The vertebral replacement implant according to claim 8,
    wherein the basket includes one or more apertures; and
    wherein the openings are sized to provide a line of sight through the openings, through the hollow interior, through the one or more apertures, and into the cavity of the basket.

12. The vertebral replacement implant according to claim 1 wherein the base of the basket comprises apertures.

13. The vertebral replacement implant according to claim 1 wherein the tubular wall is tapered.

* * * * *